United States Patent [19]

Chabardes et al.

[11] Patent Number: 5,292,897
[45] Date of Patent: Mar. 8, 1994

[54] PROCESS FOR PREPARING HALO ACETALS FROM ENAMINES

[75] Inventors: Pierre Chabardes, Sainte Foy Les Lyon; Lucette Duhamel; Pierre Duhamel, both of Mont Saint Aignan; Jerome Guillemont, Beuzeville; Jean-Marie Poirier, Saint Martin Du Vivier, all of France

[73] Assignee: Rhone-Poulenc Nutrition Animale, Commentry, France

[21] Appl. No.: 858,406

[22] Filed: Mar. 27, 1992

Related U.S. Application Data

[62] Division of Ser. No. 620,610, Dec. 3, 1990, Pat. No. 5,145,972.

[30] Foreign Application Priority Data

Dec. 1, 1989 [FR] France ................... 89 15868

[51] Int. Cl.$^5$ ............................................... C07F 9/06
[52] U.S. Cl. ................................................... 549/221
[58] Field of Search ........................................ 549/221

[56] References Cited

U.S. PATENT DOCUMENTS

| | | | |
|---|---|---|---|
| 4,087,405 | 5/1978 | Wang et al. | 549/221 |
| 4,100,201 | 7/1978 | Decor | 549/221 |
| 5,120,864 | 6/1992 | Charbardes et al. | 549/221 |

FOREIGN PATENT DOCUMENTS 1396622  6/1975  United Kingdom .

OTHER PUBLICATIONS

H. J. Hagemeyer, Jr., et al., "Reactions Of Isopropenyl Acetate," Indus. and Eng. Chem, 41(12):290–2924 (1949).

S. M. Makin et al., J. Gen. Chem. URSS, 32:1088–1092 (1962).

*Primary Examiner*—C. Warren Ivy
*Assistant Examiner*—Raymond Covington
*Attorney, Agent, or Firm*—Finnegan, Henderson Farabow, Garrett & Dunner

[57] ABSTRACT

The present invention relates to a process for preparing halo acetals of ethylenic aldehydes by reaction of a halogen cation with enamine followed by a hydrolysis and reaction with an alcohol, a glycol or an orthoformate. These halo acetals are used as intermediate for the synthesis of vitamins A and E.

It also relates to a new compound of formula (IV),

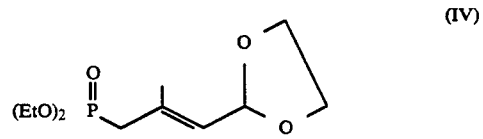

to a process for preparing it from halo acetals of ethylenic aldehydes by reaction with triethyl phosphate, and to its use for the preparation of retinal by reaction with β-ionylideneacetaldehyde.

1 Claim, No Drawings

PROCESS FOR PREPARING HALO ACETALS FROM ENAMINES

This is a division of application Ser. No. 07/620,610, filed Dec. 3, 1990, now U.S. Pat. No. 5,145,972.

This application is related to French Patent Application Nos. 89 15868, filed Dec. 1, 1989, and 90 04194, filed Apr. 2, 1990, the disclosures of which are entirely incorporated by reference herein.

BACKGROUND OF THE INVENTION

1. Field of the Invention

The present invention relates to a new process for preparing halo acetals of ethylenic aldehydes of the formula (I):

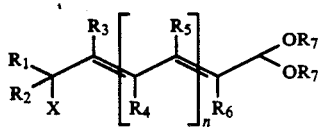

wherein:

X represents a halogen atom selected from chlorine, bromine and iodine atoms;

$R_1$, $R_2$, $R_3$, $R_4$, $R_5$ and $R_6$, which may be identical or different, represent a hydrogen atom or an alkyl radical containing 1 to 6 carbon atoms in a straight or branched chain, preferably a methyl or ethyl radical, or an alkenyl radical containing 3 to 6 carbon atoms in a straight or branched chain and in which the double bond is in a position other than 1-2;

n is equal to 0, 1, 2, 3 or 4, with the understanding that, when n is greater than 1, each $R_4$ and each $R_5$ may be identical or different; and $R_7$ each represent an alkyl radical containing 1 to 6 carbon atoms in a straight or branched chain, preferably a methyl or ethyl radical, or, together, form an alkylene radical $R'_7$ containing 2 to 6 carbon atoms in a straight or branched chain, preferably a —$CH_2$—$CH_2$— radical, and optionally substituted with a hydroxyl radical or an alkyloxy radical containing 1 to 4 carbon atoms.

It is specified that the term halogen as used hereinafter encompasses only chlorine, bromine and iodine.

2. Description of the Related Art

Halo acetals of ethylenic aldehydes are organic compounds which are especially useful as organic synthesis intermediates. Thus, according to the general process described in British Patent 1,396,622, they may be used for introducing an $\alpha,\beta$-ethylenic aldehyde unit into a mono or polyene residue by reaction with a polyene sulphone in the presence of an alkaline agent, the sulphone resulting from this condensation then being desulphonated with the formation of a further double bond.

It is known that $\gamma$-halo acetals of $\alpha,\beta$-ethylenic aldehydes may be prepared by the haloalkylation of a 1-alkyloxy-1,3-diene, by the action of an N-halosuccinimide in the presence of an alcohol according to the process described by S. M. Makin et al., J. Gen. Chem. URSS, 32:1088 (1962). The drawback of this process, however, is that the starting diethylenic ethers are difficult to prepare. The starting ethers are generally prepared by the treatment of acetals of $\alpha,\beta$- or $\beta,\gamma$-ethylenic aldehydes at high temperature in the presence of catalysts, these initial starting materials being in and of themselves difficult to synthesize. Although the method of Makin is also applicable to the synthesis of $\omega$-halo acetals of aldehydes containing a system of conjugated double bonds, the preparation of such compounds by this method presents very great problems because of the difficulty of synthesizing the necessary starting materials.

Another process is disclosed in U.S. Pat. No. 4,100,201, wherein $\omega$-halo acetals of ethylenic aldehydes are prepared by the halogenation of an ester, preferably an acetic ester, corresponding to the ethylenic aldehyde. According to the paper by H. J. Hagemeyer published in Ind. Eng. Chem. 41: 2920 (1949), this ester is prepared by exchange between the aldehyde and isopropenyl acetate. During the regeneration of the aldehyde after hydrolysis of the ester, acetic acid is liberated, thereby making it impossible to regenerate the expensive starting material, i.e., isopropenyl acetate. Thus, this process, like the Makin process above, is uneconomical.

A further process is disclosed in U.S. Pat. No. 4,087,405, wherein $\omega$-halo acetals of polyene aldehydes are prepared by the reaction of a halogen cation with an enoxysilane. Enoxysilanes are compounds which are difficult to obtain from an industrial standpoint and, as a result, are expensive starting materials.

SUMMARY OF THE INVENTION

In accordance with the novel process of the present invention, halo acetals of unsaturated aldehydes can be prepared in good yields from accessible starting materials which are inexpensive and can be readily recycled.

It has been found that the halo acetals of ethylenic aldehydes of formula (I) may be prepared by the reaction of a halogenating agent selected from the halogen cations $Cl^+$, $Br^+$ and $I^+$ with an enamine of formula (II):

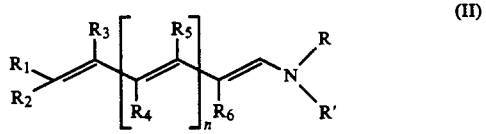

wherein $R_1$, $R_2$, $R_3$, $R_4$, $R_5$, $R_6$ and n are defined as above, and R and R' represent alkyl radicals containing 1 to 6 carbon atoms in a straight or branched chain, or an alkylene or alkenylene radical optionally containing hetero atoms selected from oxygen, sulphur and nitrogen. In particular, a piperidine or morpholine ring can be formed—and then, after water is added, the product obtained is reacted with a primary or secondary alcohol of formula $R_7OH$, with a glycol of formula HO—$R'_7$—OH, or alternatively with an orthoformate of formula $HC(OR_7)_3$, or a mixed orthoformate of formula $(O_2R'_7)CH$—$(OR_7)$ obtained by the condensation of an orthoformate $HC(OR_7)_3$ and a glycol of formula $NOR'_7OH$, wherein $R_7$ and $R'_7$ are defined as above.

Halogen cations have been known for many years, see e.g., J. Arotsky and M. C. R. Symons, Quart. Rev. 16282 (1962). It is also known that the presence of halogen cations may be demonstrated by various methods such as, e.g., conductivity measurement and mass spectrometry. Further, many products are known to be the source of such halogen cations, as for example in Peter B. D. de La Marre, "Electrophilic Halogenation", Cambridge Chemistry Texts, 1976.

In accordance with the invention, a first class of products which are usable as a source of halogen cations consists of the halogens themselves and products in which a halogen atom is linked via a covalent bond to a nitrogen, oxygen, phosphorus or sulphur atom. By way of example, preferred compounds of this class include alkali metal N-hypohalites, organic hypohalites, N-haloamines, N-haloamides, N-halocarboimides, N-halosulphoimides, N-halocarbosulphoimides, N-halohydantoins, N-halotriazoles and N-halobenzotriazoles, phosphorus oxychlorides and thionyl chloride.

A second class of products which are usable as a source of halogen cations consists of compounds resulting from the addition of molecular halogen to an aliphatic, aromatic or cyclic quaternary ammonium halide or to an aromatic halide.

A third class of products which are usable as a source of halogen cations consists of the complexes formed by the action of a molecular halogen on an aliphatic or cyclic amide.

According to the present invention, sources of halogen cations that are especially preferred are alkali metal hypohalites, organic hypohalites, especially the hypohalites of saturated tertiary aliphatic alcohols containing up to 13 carbon atoms, N-chloro- and N-bromosuccinimides, N-bromo- and N-chloropolymaleimides, N-bromo- and N-chlorocaprolactams, 1,3-dichloro- and 1,3-dibromo-5,5-dimethylhydantoins, N-bromo- and N-chlorosaccharins, chlorobenzotriazole, N-bromacetamide, bromourea, chloramine, phenyltrimethylammonium perbromide, tetrachlorotetra-n-butylammonium iodide, dichlorotetra-n-butylammonium iodide, tetra-n-butylammonium tribromide, pyridinium perbromide, iodobenzene dichloride, phosphorus oxychlorides, thionyl chloride and the complexes furnished by the action of chlorine, bromine or iodine on dimethylformamide, dimethylacetamide and N-methylpyrrolidone.

Generally speaking, it is sufficient to react one halogen cation per mole of enamine of formula (II), i.e., to use a sufficient quantity of the product generating the halogen cation to provide one halogen cation per mole of enamine of formula (II). An excess of either of these reactants, halogen cation or enamine, can be used without incurring any problems.

After the reaction between the halogen cation and the enamine of formula (II), water is added, followed by the addition of an excess of alcohol of formula $R_7OH$, or of orthoformate of formula $HC(OR_7)_3$, or of mixed orthoformate of formula $(O_2R'_7)CH-(OR_7)_3$ or, alternatively, of glycol of formula $HO-R'_7-OH$. This reaction enables the conversion of the enamine of formula (II) to a halo acetal of formula (I) to be carried out in the same reaction medium ("one pot synthesis") without isolating the intermediate products.

The temperature of the reaction is not critical, and can be, e.g., between $-70°$ and $+80°$ C., and preferably between $-60°$ and $+20°$ C. in order to avoid a significant decomposition of the products.

When the source of halogen cation is molecular halogen or compounds in which the halogen atom is linked to a nitrogen or oxygen atom, or a compound resulting from the addition of a molecular halogen to an aliphatic, aromatic or cyclic quaternary ammonium halide, or to an aromatic halide, the reaction is generally performed at a temperature of between $-70°$ C. and $+80°$ C., and preferably between $-70°$ and $+30°$ C., depending on the stability of the product used as a source of halogen cation.

If acceleration of the rate of the acetalization reaction is desired, a catalytic quantity of an inorganic or organic acid known as an acetalization catalyst, such as hydrochloric, sulphuric and methanesulphonic acids, may be advantageously introduced into the reaction mixture after reaction of the product generating the halogen cation with the enamine of formula (II).

In accordance with another aspect of the invention, when a cationic halogen, whose source is of the formula AX, is reacted with an enamine of formula (II), an intermediate iminium salt of formula (III), which is a new compound, is formed:

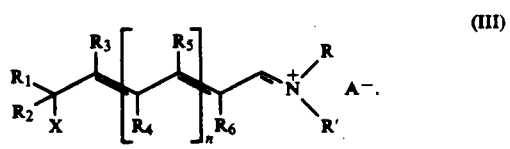
(III)

In formula (III), X, $R_1$, $R_2$, $R_3$, $R_4$, $R_5$, $R_6$, R, R' and n have the same meaning as in formulas (I) and (II), and $A^-$ represents the anion linked to the halogen cation in the source of halogen cation. $A^-$ can also thus represent a halogen X if the source of halogen cation is molecular halogen, e.g., phosphorus oxydichloride ($POCl_2^-$) or thionyl monochloride ($SOCl^-$).

In addition to compound (III), an isomeric compound (IIIA) of the following formula may also be formed:

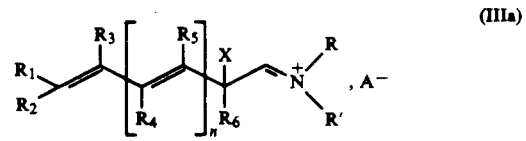
(IIIa)

which compound is readily converted to that of formula (III) by simply increasing the temperature of the reaction medium.

The enamines of formula (II) used as starting materials are prepared according to S. Hunig and H. Kahanek, Chem. Her. 90: 238 (1957), N. F. Farrell, P. W. Hickmott and B. J. Hopkins, J.C.S. (B):351 (1971), E. Demole, C. Demole and P. Enagist, Helv. Chim. Act. 59:737 (1976), all of which are incorporated by reference, by bringing the amine of formula

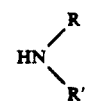

into contact with polyene aldehyde in the presence of a dehydrating agent in an aliphatic or aromatic solvent which is inert with respect to the reactants. The reactants are brought into contact at room temperature. After reaction, the dehydrating agent is removed, the solvent is removed by distillation, and the enamine is obtained by distillation.

After halogenation and acetalization, the ethylenic halo acetal of formula (I) is recovered, and the amine can be readily recycled.

The compounds of formula (I) wherein $n=0$, are used, in particular, for the synthesis of vitamin E or retinal, either by condensation directly with a sulphone containing 15 carbon atoms according to the process described in British Patent 1,396,622, incorporated herein by reference, by proceeding via a phosphonic intermediate IV which is then condensed in the presence of a base with β-ionylideneacetaldehyde.

The phosphonic intermediate (IV) is prepared by condensation of a derivative of formula (I) wherein n=0, with an alkyl phosphite.

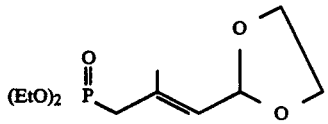

(IV)

The process according to the present invention is especially well-suited to the preparation of the dioxolane of 3-methyl-4-bromo-2-buten-1-al from 1-morpholino-3-methyl-1,3-butadiene.

To illustrate the process of the present invention, the following examples are given. It should be understood, however, that the invention is not to be limited to the specific conditions or details set forth in the examples.

EXAMPLE 1

Preparation of 3-methyl-1-morpholinobutadiene

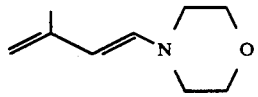

Anhydrous potassium carbonate (43.5 mmol; 6 g) and morpholine (308 mmol; 26.8 g) were introduced into a 100-ml Erlenmeyer equipped with a dropping funnel, under an inert atmosphere. When the reaction medium had been cooled to 0° C., prenal (150 mmol) in toluene (20 ml) was added dropwise. The temperature was allowed to rise to 20° C. and stirring was continued for 4 hours. The potassium carbonate was separated by filtration. The toluene was removed at atmospheric pressure, which permits cracking of the aminal. Under reduced pressure, the excess morpholine was distilled first, and then the expected dienamine (b.p. 108°-110° C. at 20 mm Hg) was distilled.

EXAMPLE 2

Preparation of 4-bromo-3-methyl-2-butenal

A solution of bromine (10 mmol; 1.6 g) in anhydrous ether (50 ml), was cooled beforehand to −70° C., and was added at a temperature below −60° C. to the dienamine (10 mmol; 1.53 g) of Example 1, dissolved in anhydrous ether (100 ml). After stirring for a quarter of an hour at −70° C., the temperature was raised to 35° C. in the course of 5 minutes. Refluxing of the ether was maintained for 15 minutes.

To characterize the (ω-bromo)iminium salt, the yellow precipitate was filtered off, protected from moisture, and then dried in a desiccator for 3 hours at room temperature in the presence of P₄O₁₀. The proton NMR spectrum, run in deuterated acetonitrile, characterized the (w-bromo)iminium salt of formula:

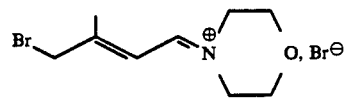

Its formation was quantitative.

¹H NMR, CD₃CN: isomer present to the extent of 25%: 9.5 (d,1H,J=11 Hz); 6.7 (d,1H,J=11 Hz); 4.7 (s,2H); 4–3.7 (m,8H); 2.2 (s,3H).

¹H NMR, CD₃CN: isomer present to the extent of 75%: 9.1 (d,1H,J=11 Hz); 7.1 (d,1H,J=11 Hz); 4.3 (s,2H); 4–3.7 (m,8H); 2.3 (s,3H).

Hydrolysis of the iminium salt was performed in the same reactor with distilled water (11 equivalents; 2 ml). The reaction medium was stirred vigorously at room temperature for two hours.

The formation of ω-bromoprenal (formula A) was checked by isolating it:

Eluant: ether/petroleum ether, 10/100.

Yld: 70%. IR: 1670 (ν C=O); 1640 (μ=C).

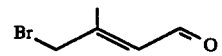

A

When the hydrolysis was performed in the reactor with water (11 equivalents; 2 ml) at −70° C., a crude product was isolated 30 minutes after the addition of bromine. The product consisted of isomeric aldehydes A and B (A/B=63:37) in a yield of 88%.

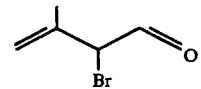

B

EXAMPLE 3

Preparation of the dioxolane of 4-bromo-3-methyl-2-butenal

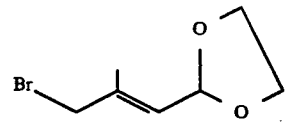

A mixed orthoformate ethylenedioxymethoxymethane (20 ml; 19 eq) and a solution (4 drops) of hydrogen chloride/ethylene glycol at a concentration of 12% by weight were introduced successively into the reaction medium obtained according to Example 2. It was necessary to stir the reaction mixture for one hour before the complete disappearance of the aldehyde in TLC was observed.

Neutralization of the medium was carried out by adding solid sodium methylate (approximately 100 mg). The medium was dried over magnesium sulphate and concentrated. A crude product (1.5 g) was recovered. After purification by flash chromatography on a silica support, a yield of 49% ω-bromo acetal was isolated.

EXAMPLE 4

Preparation of the phosphonate of the dioxolane of 3-methyl-2-butenal

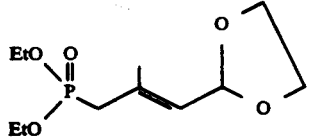

Triethyl phosphite (0.83 g; 5 mmol) in dry toluene (5 ml) and the bromodioxolane of Example 3 (1 g; 4.83 mmol) in toluene (10 ml) were introduced successively into a 25-ml two-necked flask equipped with a thermometer and a condenser.

The reaction medium was heated under toluene reflux for 15 hours.

After complete disappearance of the bromo acetal spot in TLC, the solvent was removed, and the phosphonate was purified by distillation under reduced pressure (boiling point: 110°–120 C./0.3 mm Hg). The yield of purified phosphonate was 80%.

EXAMPLE b 5

Preparation of retinal

The phosphonate of Example 4 (0.7 mmol; 0.185 g), was dissolved in THF (10 ml), and was introduced under argon into a 25-ml two-necked flask. Potassium tert-butylate (1 mmol; 0.112 g) was added in small portions at −70° C. Stirring was continued for 90 minutes at −70° C. β-Ionylideneacetaldehyde (0.5 mmol; 0.109 g), dissolved in THF (one ml), was then added. The temperature was maintained for 15 minutes at −70° C. and then 1 hour at −20° C.

Hydrolysis of the reaction medium was performed at −20° C. with 3N hydrochloric acid solution (5 ml). After stirring for a quarter of an hour, the aqueous phase was extracted with ether (5×15 ml), and the organic phase was dried over magnesium sulphate and concentrated. The crude product was purified by flash chromatography using an eluant of ether/petroleum ether in a ratio of 10:100. The yield of retinal was 66%.

What is claimed is:

1. A compound of the formula (IV):

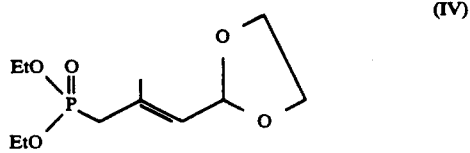

* * * * *